United States Patent
Vlaeyen et al.

[11] Patent Number: 6,093,161
[45] Date of Patent: Jul. 25, 2000

[54] THERMOPLASTIC APPARATUS WITH FASTENER

[75] Inventors: Jan Vlaeyen, Tienen; Bernard Reyter, Cerous Mousty, both of Belgium

[73] Assignee: Smith & Nephew, Inc., Memphis, Tenn.

[21] Appl. No.: 08/568,259

[22] Filed: Dec. 6, 1995

[51] Int. Cl.[7] .................................................... A61F 5/00
[52] U.S. Cl. .................................... 602/6; 602/5; 602/21
[58] Field of Search ............................................ 602/6, 21

[56] References Cited

U.S. PATENT DOCUMENTS

| | | |
|---|---|---|
| 4,060,075 | 11/1977 | Blomer et al. . |
| 4,240,415 | 12/1980 | Wartman . |
| 4,404,333 | 9/1983 | Watanabe . |
| 4,442,834 | 4/1984 | Tucker et al. . |
| 4,600,618 | 7/1986 | Raychok, Jr. et al. . |
| 4,852,556 | 8/1989 | Groiso . |
| 5,439,439 | 8/1995 | Green et al. . |

FOREIGN PATENT DOCUMENTS 0 401 883 B1   8/1994   European Pat. Off. .

Primary Examiner—John G. Weiss
Assistant Examiner—Kelvin Hart
Attorney, Agent, or Firm—Fulbright & Jaworski L.L.P.

[57] ABSTRACT

A thermoplastic apparatus and method of use for immobilization or support of a body part of a human or animal, is formed from a sheet of thermoplastic moldable material that is substantially rigid at ambient temperatures and pliable at higher temperatures. The sheet is pre-cut in a shape that generally conforms to and encircles a preselected human or animal body part with the pre-cut sheet having two opposing edges. A portion of the two opposing edges including a cooperating fastener for fastening the two opposing edges together when the pre-cut sheet encircles the preselected human or animal body part. The fastener is directly attached to the thermoplastic material, so that the fastener allows the thermoplastic apparatus to be removed from and put back on the human or animal body part and to be placed directly into a heat transfer area having a temperature between 50° C. and 100° C. for causing the apparatus to be pliable which allows the apparatus to be molded and shaped.

23 Claims, 3 Drawing Sheets

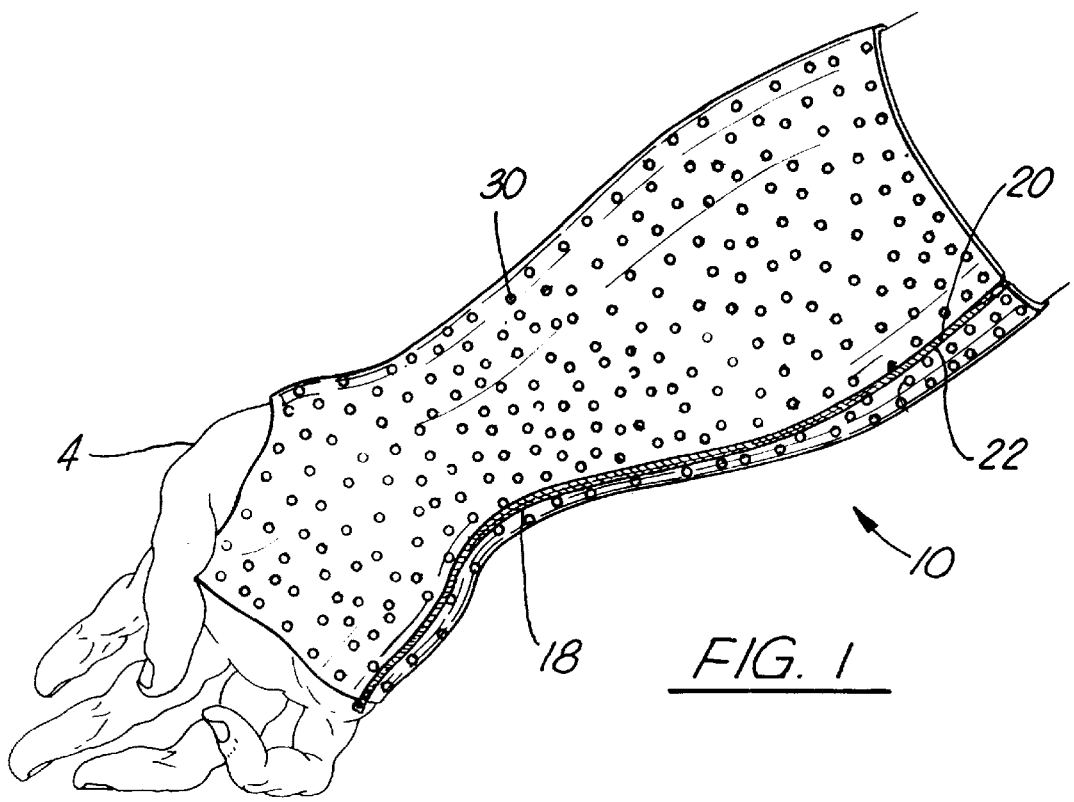
FIG. 1
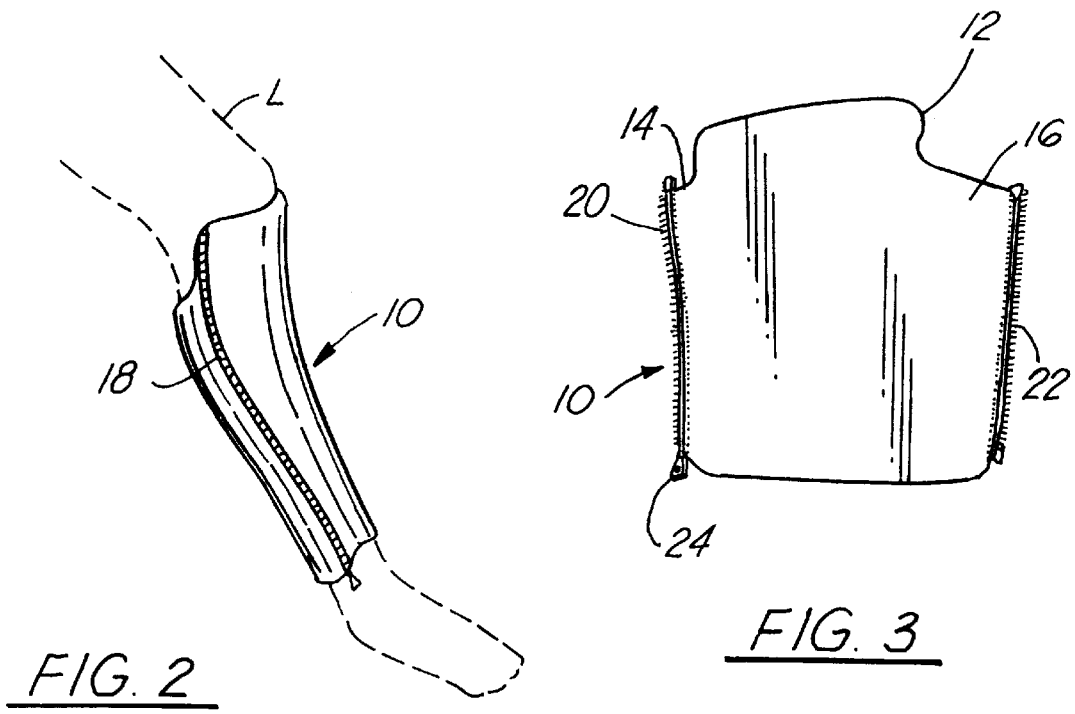
FIG. 2
FIG. 3

THERMOPLASTIC APPARATUS WITH FASTENER

FIELD OF THE INVENTION

The present invention relates to a medical immobilization device such as a cast or split formed from thermoplastic material that is moldable at temperatures between 50° C. to 100° C. for application to a body part of a human or animal and more specifically, to a thermoplastic apparatus having a directly attached fastener that allows the cast or split to be removed and reapplied to the body part.

BACKGROUND OF THE INVENTION

Immobilization devices such as casts, splints, braces and stiffening apparatus are used to impart a desired position to a supported portion of the body or to immobilize the supported portion relative to other parts of the body. Traditionally, plaster casting materials have been used because they are very low cost. However, plaster casting materials are heavy and cannot be cleaned or easily removed. Recently, plaster casting materials have been replaced by synthetic casting materials which are lighter in weight and can be cleaned but have a rough exterior surface and are still relatively heavy and bulky.

Further, both plaster of paris and synthetic resin casts require skill in wrapping techniques and there are areas of the cast where folds are unavoidable, for example in the thumb web space. Wrapped casting materials do not give as even a pressure on the body part as thermoplastic material in fracture bracing applications due to the overlaps of the casting material.

Thermoplastic materials such as those described in U.S. Pat. No. 4,240,415, are now being used for forming casts and braces and other immobilization devices. These thermoplastic materials can be produced in extruded sheets which, when brought to a melt point (50° C. to 100° C.), can be molded and manipulated to conform to and shape around a body part, such as a limb, and than allowed to cool to hardness. These materials can also be reheated, brought back to their original shape and then remolded into a different shape. Compared to other casting materials, the thermoplastic materials described in U.S. Pat. No. 4,240,415 provide many advantages including simplicity of use and ease of cleaning.

It is also often necessary that a cast or other immobilization device be removed for medical consultation or exercise by a therapist and then put back on the patient. The plaster and synthetic material casts cannot be removed intact and put back on the patient.

U.S. Pat. No. 4,060,075 describes a splinting system which is formed from a transformable material imbedded in a fabric that can include a fastener such as a zipper or a pile and loop material. In this splinting system, a two component plastic is mixed and molded in a double walled fabric that is then installed around the body part before the plastic mixture hardens. It is difficult to obtain an even cast thickness and cast surface with this splinting system and when the cast hardens it is very stiff and has no elasticity. Further, the cast cannot be reused and cannot be perforated in order to provide for ventilation.

European patent application No. 401 883 describes a thermoplastic immobilization device made from a thermoplastic extrudable molding material that is surrounded by a fabric that has a zipper on two opposite sides of the cast or splint. A commercial embodiment of EP 401,883 is known as ORFZIP which consists of a thermoplastic material within a stockinette type fabric with a zipper. The device is vacuum packed in plastic in order to prevent the stockinette from getting wet when melting the thermoplastic material. The vacuum packed device is placed in water at a temperature required to soften the thermoplastic material so that it can be molded. Once the plastic packaging is opened, the cast cannot be reworked without getting the stockinette wet or the risk of burning the fabric with a heat gun. Also, the supple material or stockinette type fabric has a tendency to detach from the thermoplastic material and bunch up in areas which are stretched and molded, which causes potential pressure problems to the patient when the cast is in place. Further, the thermoplastic material is very sticky when softened which makes molding difficult.

The present invention seeks to remedy the aforementioned problems and drawbacks of the currently available immobilization devices. The invention resides in the combination of parts set forth in the specification and defined by the claims and provides a pre-cut thermoplastic immobilization apparatus with a directly attached fastener that allows the apparatus to be reapplied after removal and to be placed directly into a heat transfer area having the temperature of between 50° C. to 100° C. for causing the apparatus to be pliable.

SUMMARY OF THE INVENTION

The present invention provides a thermoplastic apparatus and its method of use for immobilization or support of a body part of human or animal that comprises a sheet of thermoplastic moldable material that is substantially rigid at ambient temperatures and pliable at higher temperatures. The sheet is pre-cut in a shape that generally conforms to and encircles a pre-selected human or animal body part with the pre-cut sheet having two opposing edges. A portion of the two opposing edges includes a cooperating fastening means for fastening the two opposing edges together when the pre-cut sheet encircles the pre-selected human body part. The fastening means is directly attached to the thermoplastic material which allows the thermoplastic apparatus to be removed from the limb or body part and put back on the human or animal body part. Because the fastening means is directly attached to the thermoplastic material, the apparatus can be placed directly into a heat transfer area having a temperature between about 50° C. to 100° C. so as to cause the apparatus to be pliable, thus avoiding the problems involved with other types of casting material or thermoplastic casts which are covered with fabric.

BRIEF DESCRIPTION OF THE DRAWINGS

The invention will become more apparent when the detailed description of exemplary embodiment is considered in conjunction with the appended drawings, in which:

FIG. 1 is a perspective view of the present invention applied to an arm of a human;

FIG. 2 is a perspective view of the present invention applied to a portion of a leg of a human;

FIG. 3 is a plan view of the exterior surface of a pre-cut apparatus of the present invention that generally conforms to a portion of a hand and thumb of a human;

DETAILED DESCRIPTION OF PREFERRED EMBODIMENT

Thermoplastic materials soften under heat, are capable of being molded and shaped with hand pressure, and harden on cooling without undergoing chemical changes. A thermoplastic material, suitable for use as a casting or immobilization device, should soften at sufficiently low temperatures so as to allow for molding directly on the patient without injury due to scalding or burning of the skin. Suitable polymers which melt or soften at temperatures ranging from 50° C. to 100° C. include poly (ethyleneadipate), poly (epsilon-caprolactone), polyvinyl stearate, cellulose acetate, butyrate and ethyl cellulose poly (propylene oxide) containing comonomers, trans polyisoprene and cis polyisoprene based thermoplastic materials, and polycaprolactone based materials including commercially available polycaprolactone thermoplastic materials known as AQUAPLAST, SYNERGY, EZEFORM, POLYFORM and POLYFLEX II. These thermoplastic materials are available from Smith & Nephew Roylan Inc., N104, W13400 Donges Bay Road, Germantown, Wis. 53022.

A thermoplastic immobilization apparatus 10 can be made according to the method claimed in U.S. Pat. No. 4,240,415, incorporated herein by reference. This patent describes a thermoplastic material formed from a thermoplastic polyester having a melting point between about 50° C. and 100° C., and more particularly a poly (epsilon-caprolactone) having a weight average molecular weight of over 5,000 with a half time crystallization at 36° C. of between 0.5 and 10 minutes. At room temperature the poly (epsilon-caprolactone) is quite stiff with a 1% secant modulus of 50,000 psi at 23° C. The stiffness remains high as the temperature is increased. At 60° C. some melting occurs and the stiffness modulus is 20,000 psi. Additionally, some of the poly (epsilon-caprolactone) mixtures become transparent when heated which is useful when molding and placing a casting device on a limb or other body part of a human patient. The thermoplastic material also has 100% elastic memory which allows it to be reheated and reshaped repeatedly.

Figure 5:
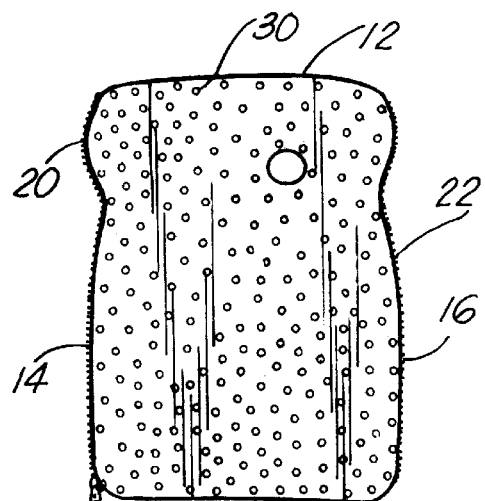
FIG. 5 is a plan view of the exterior surface of a pre-cut apparatus of the present invention that generally conforms to a portion of a hand of a human.
Figure 6:
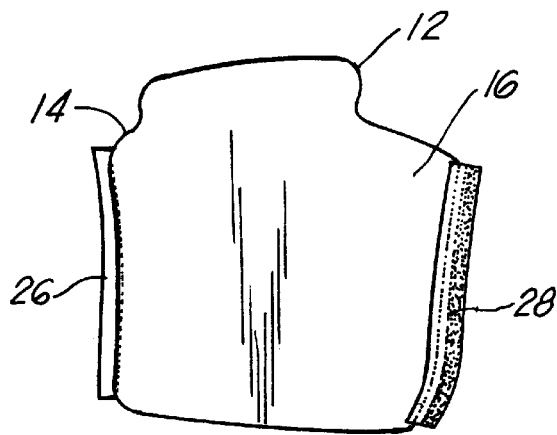
FIG. 6 is a plan view of the exterior surface of a pre-cut apparatus of the present invention that generally conforms to another portion of a hand of a human.
Figures 7, 8:
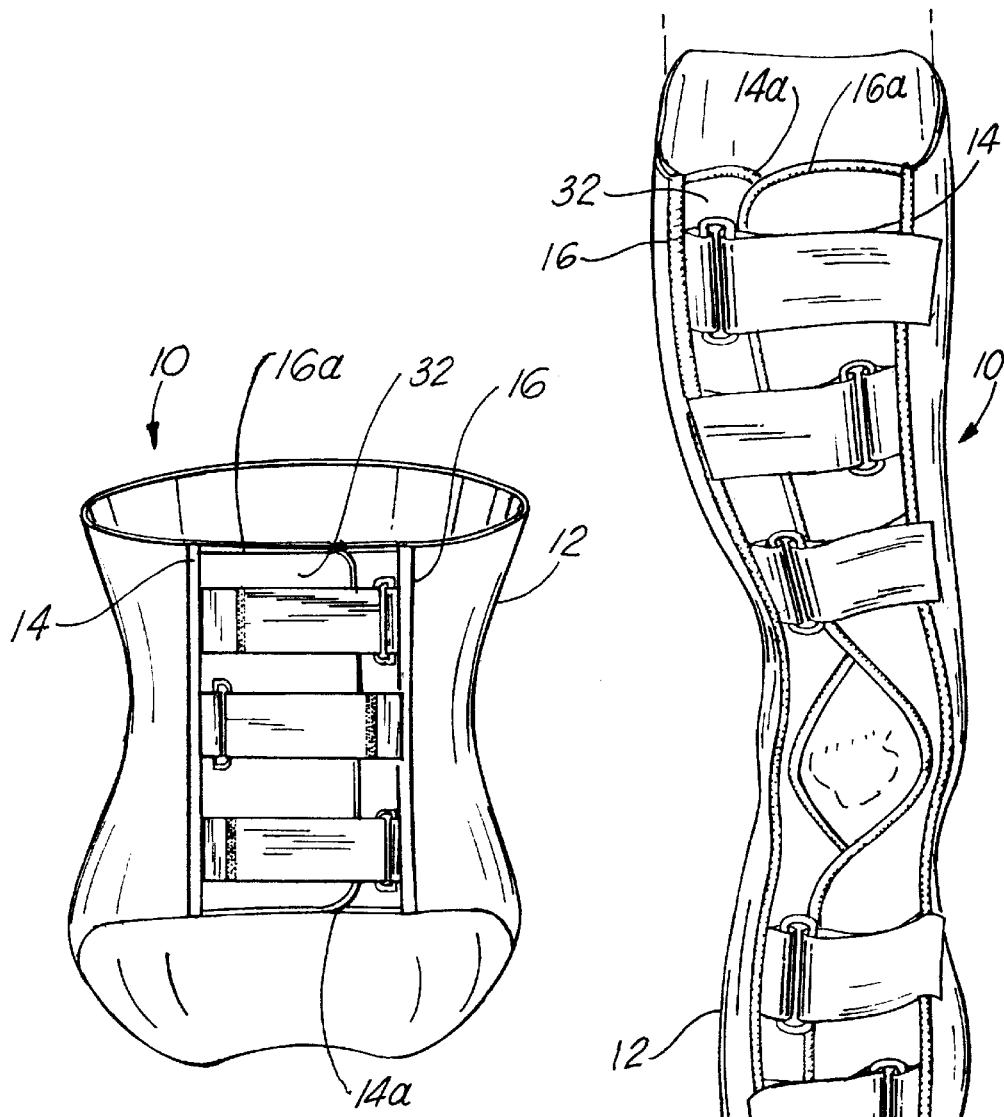
FIG. 7 is a perspective view of the present invention applied to the torso of a human.
FIG. 8 is a perspective view of the present invention applied to a portion of a leg of a human.

In a preferred embodiment the thermoplastic material is pre-cut in a shape that generally conforms to and encircles a preselected human body part, as illustrated in FIGS. 3–6. A pre-cut sheet 12 has two long opposing edges 14, 16 which come together when the pre-cut sheet 12 is placed on a body part of a human patient and encircles a limb or body part as illustrated in FIGS. 1 and 2. All or a major portion of the two opposing edges 14, 16 includes a cooperating fastener 18 for fastening the two opposing edges 14, 16 together when the pre-cut sheet 12 encircles a preselected human body part H or limb L, as illustrated in FIGS. 1 and 2. The fastener 18 has two cooperating sides 20, 22 which are attached directly to the pre-cut sheet 12, for example by sewing or gluing the sides 20, 22 of the cooperating fastener 18 to the long opposing edges 14, 16 of the pre-cut sheet 12. The fastener can also be attached to the pre-cut sheet 12 by heat or laser welding, stamping, chemical bonding or other suitable means. The fastener 18 can be either a zipper 24 (FIGS. 3–5) or a strip of loop pile material 26 that is fastened to one of the opposing edges 14 and a strip of hook gender material 28 is fastened to the other opposing edge 16 (FIG. 6). The hook gender material 28 is adapted to engage the loop pile material 26. A fastener of this type is typically known commercially as either VELFOAM or VELCRO but it can be known under other brand names as well. The zipper 24 or the loop and hook material 26, 28 can be sewn directly to the thermoplastic material of the pre-cut sheet 12 by an industrial sewing machine in which either nylon, cotton or polyester thread can be used. In a preferred embodiment, nylon is the thread that is used to attach the fastener 18 to the opposing edges 14, 16 of the thermoplastic pre-cut sheet 12. A portion of foam material 32 can also be placed between the opposing edges 14, 16, as illustrated in FIGS. 7 and 8, in which the fastener is attached to opposing edges 14a, 16a of the foam material 32.

The thickness of the thermoplastic material is at least 1.5 mm and will generally be less than about 8 mm. In a preferred embodiment, the thickness of the thermoplastic material will be generally from about 1.5 mm to 3.5 mm with the thickness typically being about 2.4 mm. When the thermoplastic material is used for an immobilization apparatus of the hand, the thinner material is preferable and when the thermoplastic material is used as an immobilization apparatus for the lower extremities, the thicker thermoplastic material is preferred. A variety of thicknesses of thermoplastic material can be formed into sheets in which the appropriate thickness is chosen for the desired support of the pre-selected body part. Selecting a sheet of the appropriate thickness will eliminate excess bulk in the weight of the immobilization apparatus 10.

In a preferred embodiment the sheets of thermoplastic material are perforated prior to cutting the sheets into the desired shape. Perforations 30 permit ventilation of the skin when the apparatus is placed upon a body part of a human patient. Preferably, between about 38–42% of the total surface area of the apparatus is perforated. This amount of perforation will provide adequate strength to the apparatus while allowing for good air circulation which will improve skin ventilation as compared to unperforated sheets. The diameter of the perforations 30 is generally in the range of about 1.6 to 3.2 mm with preferred diameter to be generally about 2.5 mm. Alternatively, perforations over a smaller percentage of surface area will provide only slight ventilation.

When in use as an immobilization apparatus, the immobilization apparatus 10 of the present invention is typically applied over a stockinette liner (not shown) placed directly on the limb or body part to be treated. The stockinette should be worn during molding but its use is optional after the apparatus hardens. The stockinette absorbs perspiration and prevents any allergic reactions which may occur when the immobilization apparatus 10 is used alone. Further, stockinette formed from a high quality jersey or similar stockinette material can be changed and cleaned independently of the immobilization apparatus.

Figure 4:
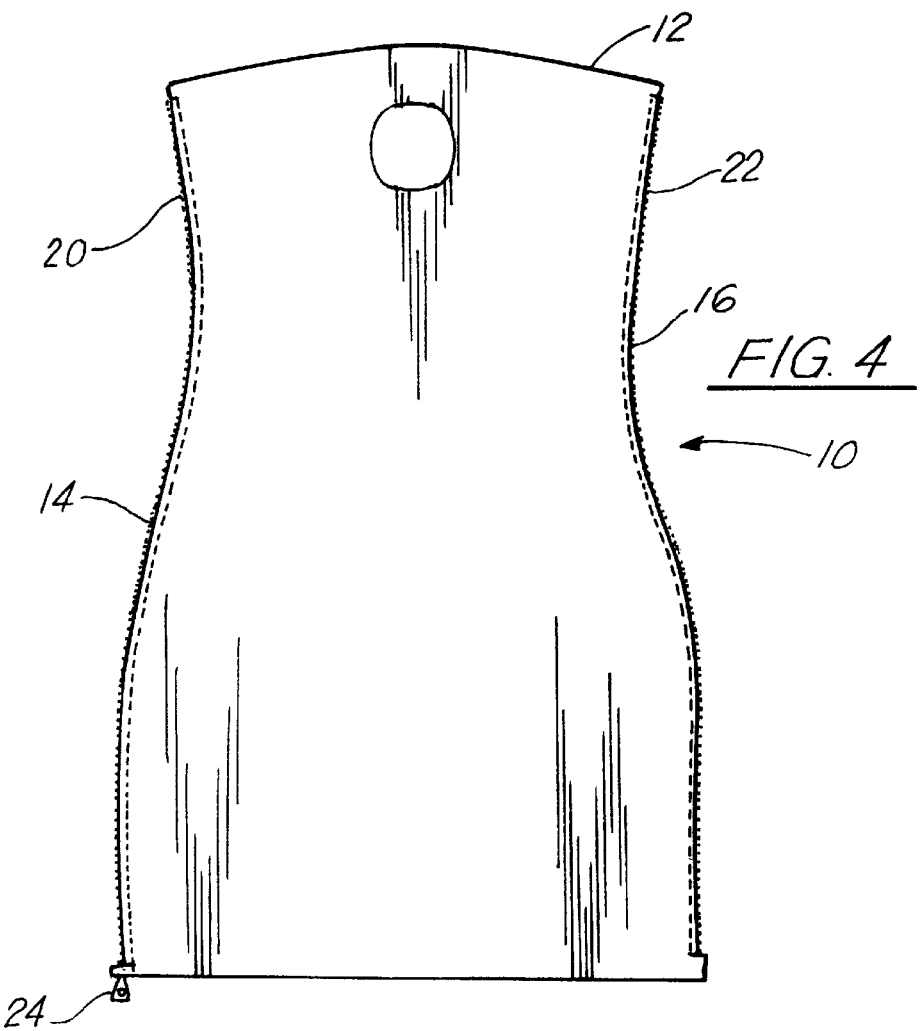
FIG. 4 is a plan view of the exterior surface of the present invention as shown in FIG. 1.

The immobilization apparatus 10 of the present invention can be used for tendon repairs and fractures and it can also be used for stabilization following sprains and strains, and in the presence of arthritis, tendinitis and cumulative trauma injuries. The immobilization apparatus 10 can also be used for a wide variety of casts, splints and braces including wrist splints, cervical collars, lumbosacral immobilizers, upper and lower extremity supports, thoracic supports, knee immobilizers, ankle braces and is therefore not intended to be limited by the following examples shown in FIGS. 1–6 of the drawings. FIGS. 1, 4 and 5 illustrate generally typical pre-cut shapes for wrist splints, FIG. 2 illustrates a generally typical lower leg support, FIG. 3 illustrates a generally typical pre-cut wrist and thumb spica splint, and FIG. 6 illustrates a generally typical pre-cut wrist and thumb spica splint with IP immobilization. A range of sizes of the immobilization apparatus 10 can be produced, for example from extra small to extra large so as to enable the apparatus 10 to be able to generally conformed to and encircle a pre-selected human or animal body part.

The immobilization apparatus 10, as illustrated in FIGS. 1–6, is manufactured by taking a 2.4 mm sheet of poly (epsilon-caprolactone) material prepared according to the method claims in U.S. Pat. No. 4,240,415 and cut in a selected shape as shown in FIGS. 3–6. A zipper fastener 24 or other fastener 18 can be sewn to the two opposing edges 14, 16 with nylon thread using an industrial sewing machine. The apparatus 10 is used by softening the pre-cut sheet 12 in a heat transfer area, preferable water, having a temperature of between 50° C. to 100° C. and more preferably about 65–75° C., for 1 minute until the sheet 12 becomes transparent. Depending upon the type and thickness of the thermoplastic material used, the time the apparatus 10 remains in the heat transfer area can range from about 1 to 8 minutes. Further, not all types of the thermoplastic material become transparent. The pre-cut apparatus 10 is then partially molded and shaped around the selected limb or body part and secured in place by zipper fastener 24 as illustrated in FIG. 4 or 5 or the loop and hook material 26, 28 as illustrated in FIG. 6. After the apparatus 10 is secured around the selected limb or body part, the apparatus is molded and shaped to a final fit that conforms to the configuration of the selected limb or body part and allowed to cool and harden in the final shape. The immobilization apparatus 10 hardens in place and cools after about 5 to 10 minutes of molding time by a technician. If perforations 30 are desired in the immobilization apparatus 10, the perforations are formed by punching out holes in the pre-cut sheets 12 before the fastener 18 is sewn in place. In a preferred embodiment, generally about 38–42% of the total surface area of the apparatus is perforated in order to provide ventilation. Once the apparatus 10 hardens into the molded position, it can be easily and repeatedly reheated and reformed to conform to the pre-selected body part. The fastener 18 allows apparatus 10 to be easily removed and reapplied and to be placed directly into a heat transfer area having a temperature of between 50° C. to 100° C. so as to become pliable. The attachment of the fastener 18 to the pre-cut sheet 12 prior to molding and shaping the apparatus 10 allows both the sheet 12 and the fastener 18 to be molded and shaped as one piece which provides for a better conforming fit of the apparatus 10 to the selected limb or body part.

The immobilization apparatus 10 made in accordance with the invention offers the advantage of being able to be removed and reapplied to a human body part without cutting or reheating the apparatus. Because the fastener is directly attached to the sheet 12, the immobilization apparatus 10 can be heated and made pliable by placing the apparatus directly into the heat transfer area, such as water, thus avoiding the problems involved with other types of casting material or thermoplastic casts which are covered with fabric. Although the present invention has been described with reference to its preferred embodiments, those skilled in the art will recognize changes which may be made in form or structure which do not depart from the spirit of the invention already described in the specification and embodied in the claims which follow.

What is claimed is:

1. A medical thermoplastic apparatus for immobilization or support of a body part of a human or animal comprising:
    a pre-cut sheet of thermoplastic moldable material that is substantially rigid at ambient temperatures and pliable at higher temperatures of between about 50° C. to about 100° C., said pre-cut sheet having opposing edges and shaped to generally conform to and encircle a selected human or animal body part when in the pliable state,
    a fastener for fastening the opposing edges of the sheet, said fastener adapted to help shape and hold the sheet in a configuration generally conforming to and encircling said body part when said sheet is in a pliable state, and adapted to cause said sheet to supply generally even pressure to said body part when in the rigid state,
    whereby said pre-cut sheet hardens into a substantially rigid configuration generally conforming to and encircling said body part and also supplying generally even pressure to said body part.

2. The medical thermoplastic apparatus of claim 1, wherein the fastener is directly attached to the thermoplastic material and adapted to allow the thermoplastic apparatus to be removed from and put back on said body part.

3. The medical thermoplastic apparatus of claim 2, wherein the attachment of the fastener directly to the thermoplastic material allows the apparatus to be placed directly into a heat transfer area having a temperature of between about 50° C. to about 100° C. for causing the apparatus to become pliable and capable of being molded and shaped into a conforming configuration.

4. The thermoplastic apparatus of claim 1, wherein the fastener includes a zipper.

5. The thermoplastic apparatus of claim 1, wherein the fastener is formed of a strip of loop pile material fastened to one of the opposing edges and a strip of hook gender material fastened to the other opposing edge, the hook gender material being adapted to engage the loop pile material.

6. The thermoplastic apparatus of claim 1, wherein the fastener is directly attached to the pre-cut sheet by sewing the fastener in place.

7. The thermoplastic apparatus of claim 1, wherein the thermoplastic material is between about 1.5 to about 3.5 mm thick.

8. The thermoplastic apparatus of claim 1, wherein the pre-cut sheet of thermoplastic material has perforations in generally about 38 to about 42% of its total surface area.

9. The thermoplastic apparatus of claim 8, wherein the perforations in the pre-cut sheet are between about 1.6 to about 3.2 mm in diameter.

10. The thermoplastic apparatus of claim 1, wherein the thermoplastic material is selected from the group consisting of polycaprolactones, particularly, poly(epsilon-caprolactone), poly(ethyleneadipate), polyvinyl stearate, cellulose acetate, butyrate, ethyl cellulose, poly(propylene oxide), trans polyisoprene and cis polyisoprene, or any of these materials containing fillers.

11. A method of using a thermoplastic apparatus for immobilization or support of a body part of a human or animal, comprising the steps of:
    (a) selecting a pre-cut sheet of thermoplastic moldable material that is substantially rigid at ambient temperatures and pliable at higher temperatures of between about 50° C. to about 100° C., the pre-cut sheet having two opposing edges and capable of being shaped into a configuration that generally conforms to and encircles a preselected human or animal body part when in the pliable state, and capable of supplying generally even pressure to said body part when in the rigid state, the sheet including a cooperating fastener attached directly to the opposing edges for fastening the opposing edges together;

(b) placing the apparatus directly into a heat transfer area having a temperature of between about 50° C. to about 100° C. for causing the apparatus to become pliable;

(c) removing the apparatus from the heat transfer area when the apparatus becomes pliable, generally after about 1 to 8 minutes;

(d) placing the apparatus around the preselected body part and partially molding and shaping the apparatus to conform to and encircle said body part;

(e) securing the two opposing edges of the apparatus together with the cooperating fastener;

(f) completing the molding and shaping of the apparatus into a conforming configuration encircling the preselected body part; and (g) allowing the apparatus to cool and harden, wherein said body part is subjected to generally even pressure from said apparatus.

12. The method of claim 11, wherein the temperature of the heat transfer area is between about 65° C. to about 75° C.

13. The method of claim 11, wherein the fastener of the thermoplastic apparatus includes a zipper.

14. The method of claim 11, wherein the fastener of the thermoplastic apparatus is formed of a strip of loop pile material fastened to one of the opposing edges and a strip of hook gender material fastened to the other of the opposing edges, the hook gender material being adapted to engage the loop pile material.

15. The method of claim 11, wherein the fastener is directly attached to the pre-cut sheet by sewing the fastener in place.

16. The method of claim 11, wherein a stockinette liner is placed over the body part prior to placing the apparatus around the body part.

17. The method of claim 11, wherein the thermoplastic material is selected from the group consisting of polycaprolactones, particularly, poly(epsilon-caprolactone), poly(ethyleneadipate), polyvinyl stearate, cellulose acetate, butyrate, ethyl cellulose, poly(propylene oxide), trans polyisoprene and cis polyisoprene, or any of these materials containing fillers.

18. A medical thermoplastic apparatus for immobilization for support of a body part of a human or animal, comprising:

a sheet of thermoplastic moldable material that is substantially rigid at ambient temperatures and pliable at higher temperatures of between about 50° C. to about 100° C. in order to allow the apparatus to be molded and shaped into a conforming configuration, the sheet being pre-cut in a shape that is capable of generally conforming to and encircling a selected human or animal body part when in the pliable state, and capable of supplying generally even pressure to said body part when is the rigid state, the pre-cut sheet having two opposing edges;

a section of non-thermoplastic material being attached to each of the two opposing edges, the material being sized and shaped so as to allow each section of material to substantially overlap each other;

a portion of the two opposing edges further including cooperating fasteners positioned over the overlapping sections of material for fastening the two opposing edges together and for shaping and holding the sheet in a configuration which generally encircles the preselected body part when in the pliable state, and which supplies generally even pressure to said body part when in the rigid state, said cooperating fasteners including straps having a portion of loop pile material and a portion of hook gender material, the hook gender material being adapted to engage the loop pile material;

wherein the cooperating fasteners and the sections of non-thermoplastic material are directly attached to the thermoplastic material and allow the thermoplastic apparatus to be removed from and placed back on the body part.

19. The thermoplastic apparatus of claim 18, wherein the non-thermoplastic material is a foam material.

20. The thermoplastic apparatus of claim 18, wherein the thermoplastic material is between about 1.5 to about 3.5 mm thick.

21. The thermoplastic apparatus of claim 18, wherein the pre-cut sheet of thermoplastic material has perforations in generally about 38 to about 42% of its total surface area.

22. The thermoplastic apparatus of claim 21, wherein the perforations in the pre-cut sheet are between about 1.6 to about 3.2 mm in diameter.

23. The thermoplastic apparatus of claim 18, wherein the thermoplastic material is selected from the group consisting of polycaprolactones, particularly, poly(epsilon-caprolactone), poly(ethyleneadipate), polyvinyl stearate, cellulose acetate, butyrate, ethyl cellulose, poly(propylene oxide), trans polyisoprene and cis polyisoprene, or any of these materials containing fillers.

* * * * *